(12) United States Patent
Lee

(10) Patent No.: US 6,284,856 B1
(45) Date of Patent: Sep. 4, 2001

(54) ACRYLATE, SILICONE, STYRENE, URETHANE COPOLYMER COATINGS FOR NATURAL AND SYNTHETIC RUBBER ARTICLES

(75) Inventor: Ivan S. Lee, Arcadia, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/215,578

(22) Filed: Dec. 17, 1998

Related U.S. Application Data

(63) Continuation-in-part of application No. 08/878,144, filed on Jun. 18, 1997, now Pat. No. 5,993,923, which is a continuation-in-part of application No. 08/389,571, filed on Feb. 14, 1995, now abandoned.

(51) Int. Cl.[7] ................................................. C08F 220/12
(52) U.S. Cl. ...................... 526/329.2; 526/301; 526/321; 526/324; 526/325; 526/328.5; 526/329; 526/347; 428/36.8; 428/451; 428/492; 428/520; 428/522
(58) Field of Search ................................. 526/301, 321, 526/324, 325, 328.5, 329, 329.2, 347; 428/36.8, 451, 492, 520, 522

(56) References Cited

U.S. PATENT DOCUMENTS

| | | | |
|---|---|---|---|
| 2,795,564 | 6/1957 | Conn et al. | 524/762 |
| 3,025,403 | 3/1962 | Belknap et al. | 250/516.1 |
| 3,185,751 | 5/1965 | Sutton | 264/301 |
| 3,255,492 | 6/1966 | Velonis et al. | 425/275 |
| 3,286,011 | 11/1966 | Kavalir et al. | 264/306 |
| 3,411,982 | 11/1968 | Kavalir et al. | 428/493 |
| 3,808,287 | 4/1974 | Thomas | 528/26 |
| 3,813,695 | 6/1974 | Podell, Jr. et al. | 2/168 |
| 3,856,561 | 12/1974 | Esemplare et al. | 428/494 |
| 3,933,702 | 1/1976 | Caimi et al. | 524/44 |
| 3,959,554 | 5/1976 | Hick | 428/336 |
| 4,027,060 | 5/1977 | Esemplare et al. | 428/212 |
| 4,082,862 | 4/1978 | Esemplare et al. | 427/133 |
| 4,302,852 | 12/1981 | Joung | 2/167 |
| 4,304,008 | 12/1981 | Joung | 2/167 |
| 4,310,928 | 1/1982 | Joung | 2/161.7 |
| 4,752,639 | 6/1988 | Haller et al. | 525/66 |
| 4,826,907 | 5/1989 | Murao et al. | 524/394 |
| 4,994,538 | 2/1991 | Lee | 526/279 |
| 5,026,448 | 6/1991 | Reafler et al. | 156/212 |
| 5,069,965 | 12/1991 | Esemplare | 428/330 |
| 5,084,514 | 1/1992 | Szczechura et al. | 525/123 |
| 5,171,809 | 12/1992 | Hilty et al. | 526/279 |
| 5,202,368 | 4/1993 | Davies et al. | 524/266 |
| 5,214,095 | 5/1993 | Lavoie | 524/806 |
| 5,216,057 | 6/1993 | Pratt et al. | 524/269 |
| 5,234,736 | 8/1993 | Lee | 428/42 |
| 5,306,558 | 4/1994 | Takahashi et al. | 428/331 |
| 5,534,350 | 7/1996 | Liou | 428/423.1 |
| 5,571,219 | * 11/1996 | Gorton | 2/161.7 |
| 5,603,996 | * 2/1997 | Overcash et al. | 428/34.2 |
| 5,661,208 | 8/1997 | Estes | 524/457 |
| 5,691,069 | 11/1997 | Lee | 428/500 |
| 5,700,585 | 12/1997 | Lee | 428/500 |
| 5,712,346 | 1/1998 | Lee | 525/288 |

FOREIGN PATENT DOCUMENTS

| | | |
|---|---|---|
| 2128670 | 2/1995 | (CA) . |
| 9105657 | 5/1991 | (EP) . |
| 0455323 | 11/1991 | (EP) . |
| 0543657 | 5/1993 | (EP) . |
| 0544569 | 6/1993 | (EP) . |
| 0640623 | 3/1995 | (EP) . |
| 9529196 | 11/1995 | (EP) . |
| 9625279 | 8/1996 | (EP) . |
| 0757059 | 2/1997 | (EP) . |
| 2272156 | 12/1975 | (FR) . |
| 806142 | 12/1956 | (GB) . |
| 1052546 | 12/1966 | (GB) . |
| WO84/00908 | 3/1984 | (WO) . |

OTHER PUBLICATIONS

J. S. Sadowski, B. Martin & D. D. Gerst; *Polyurethane Latexes for Coagulation Dipping*; Aug. 1978; pp. 14–17.
T. D. Pendle, & A. D. T. Gorton; *Dipping With With Natural Rubber Latex*, pp. 1–12, Feb. 1995 (Fax Date).
Russell D. Culp & Bradley L. Pugh; *Natural Rubber Dipping Technologies*, Apr. 6 & 7, 1989, pp. 1–15.

\* cited by examiner

*Primary Examiner*—Helen L. Pezzuto
(74) *Attorney, Agent, or Firm*—Christie, Parker & Hale, LLP

(57) ABSTRACT

Rubber articles are coated with a powder-free copolymer coating to provide improved mold release characteristics, improved donning characteristics, and improved tactile feel. The copolymer is formed by the polymerization of a low surface energy monomer, an alkyl acrylate, a hard monomer and a urethane oligomer. The copolymers are preferably formed by a sequential polymerization process.

12 Claims, 6 Drawing Sheets

ACRYLATE, SILICONE, STYRENE, URETHANE COPOLYMER COATINGS FOR NATURAL AND SYNTHETIC RUBBER ARTICLES

CROSS REFERENCE TO RELATED APPLICATIONS

This application is a continuation-in-part of application Ser. No. 08/878,144, filed Jun. 18, 1997, now U.S. Pat. No. 5,993,923 which is a continuation-in-part of application Ser. No. 08/389,571, filed Feb. 14, 1995, abandoned. The entire contents of both applications are incorporated herein by this reference.

FIELD OF THE INVENTION

The invention relates to articles formed of natural or synthetic rubber having thereon a powder-free polymeric coating that enables or enhances mold- or substrate-stripping and donning.

BACKGROUND OF THE INVENTION

Rubber articles made from natural or synthetic rubber include surgical gloves, physician examining gloves, industrial work gloves, prophylactics, catheters, balloons, tubing, sheeting and the like. Some of these articles, and in particular gloves, require the ability of donning, that is, the ability of the rubber article to be slid on and off skin surfaces without undue clinging or friction. Surgical gloves require wet donning, that is, the ability to be slid over wet skin surfaces, while physician examining and industrial work gloves require the ability to be slid over dry skin surfaces. Other rubber articles, like catheters and tubing, require some means to isolate the rubber from body fluids and tissue.

While this invention pertains to polymeric coatings for all rubber articles, discussion of the invention will focus on gloves, which are the most complex of rubber articles in terms of use and manufacture. To achieve acceptable donning properties, the surface of rubber a glove that comes in contact with skin or tissue has to be modified to reduce friction.

Surgeons' gloves, as of today, desire the donning surface to be sufficiently hydrophilic to absorb moisture that may be present on the surface of skin or tissue when the article is donned. Hydrogel coatings, as described, for instance, in U.S. Pat. No. 3,813,695, incorporated herein by reference, have been employed to achieve this property.

Examination and other gloves, by contrast, do not have a hydrophilicity requirement but still require the ability of the rubber article to be slid over dry skin surfaces with minimal drag or friction. Traditionally, this had been achieved by applying talc or other powdered materials, such as modified corn starch, over the skin or tissue-contacting surface of the glove. However, talc can no longer be used, and other powders can contaminate the field of work. The same problems arise for gloves used by workers in dust-free environments, such as clean rooms used in the manufacture of computer chips and other electronic articles.

With reference to FIG. 1, the conventional way of manufacturing rubber gloves has been to dip a mold or former, having the shape of the article to be formed, into a powder/coagulant slurry containing calcium nitrate and calcium carbonate. After drying, the mold is immersed in a rubber emulsion (latex) for a time sufficient for the rubber to coagulate and form a coating of desired thickness. The formed coagulated rubber article is then oven-cured. Water leaching is generally employed as the next step in order to remove rubber impurities. Once the leaching process has been completed, the rubber article is then dipped into a starch slurry. The starch-coated surface is then dried to provide a powder coat on the surface of the glove. After cooling, the rubber article is stripped from the mold. This turns the glove inside out. The mold is then cleaned and recycled.

Methods and materials used for glove manufacture are described, for instance, in U.S. Pat. Nos. 3,411,982 and 3,286,011 to Kavalier et al., both incorporated herein by reference, "Polyurethane Latexes for Coagulation Dipping," Sadowski et al., Elastomerics, August 1979, pp. 17–20, incorporated herein by reference, and "Dipping with Natural Rubber Latex," Pendler et al., Natural Rubber Technical Bulletin, 1980, also incorporated herein by reference.

Halogenation, for example, chlorination, and other chemical surface treatments have been used to eliminate the need for a powder coat that improves the dry donning characteristics of the final product. While effective, such treatments are expensive and have the shortcoming of reducing the shelf life of the rubber articles formed. It would be desirable to provide a rubber article with a powder-free donning surface without resorting to the expensive and article-deteriorating practices now popular. Such a process could substantially reduce the cost of manufacture and maximize the shelf life of the rubber article.

U.S. Pat. No. 4,302,852 to Joung, incorporated herein by reference, proposed covalently bonding an RTV silicone coating to the interior surface of a rubber surgeons glove after formation of the glove. This is said to reduce but not eliminate the need for a donning powder.

U.S. Pat. No. 4,304,008 also to Joung and incorporated herein by reference, applies a covalently bonded silicone or urethane to the outer surface of the glove, and halogenates the inner surface. The halogenated inner surface eliminates the need for a donning powder.

U.S. Pat. No. 4,310,928, also to Joung and incorporated herein by reference, teaches the deposition of a lipo compound (lipid or lipophilic substances) in place of a powder of mineral origin in combination with a surfactant in a coagulant solution to form a uniform film on a glove mold onto which the rubber is coagulated. The lipo compound and surfactant enable stripping of a formed glove from its mold.

These and other proposals have not achieved commercial acceptance.

SUMMARY OF THE INVENTION

The present invention provides acrylic-based copolymers to coat, firmly adhere to, and in some instances, be absorbed on the surface of a rubber article. The copolymers may either be deposited as a slurry during the coagulation of the rubber article, or deposited onto a preformed rubber article. The copolymers improve the properties of mold-stripping (release from the mold) of the formed rubber article. They also improve the dry and wet donning characteristics of the rubber article, without requiring further chemical treatment. Such donning characteristics and mold stripping properties may be achieved by depositing the same or a different acrylic-based copolymer on opposed surfaces of the formed rubber article.

The acrylic-based copolymers of the present invention are preferably emulsion-based copolymers polymerized from a monomer mixture that includes at least one reactive (copolymerizable) low surface energy monomer, preferably a silicone oligomer; at least one alkyl acrylate; at least one reactive (copolymerizable) aliphatic urethane oligomer; and at least one reactive (copolymerizable) hard monomer. As used herein, the term "monomer mixture" refers to a mixture of monomers and/or oligomers that can be copolymerized to form the desired copolymer. The hard monomers (described below) should be present in a total amount sufficient to form a non-tacky copolymer directly or by blending of copolymers. Preferably, a sequential polymerization process using two different monomer mixture emulsions is used to produce the coating emulsion. The first monomer mixture should yield a first copolymer that exhibits at least one dominant glass transition temperature ($T_g$) peak below about 0° C., while the second monomer mixture should yield a second copolymer exhibiting at least one dominant glass transition temperature peak above about 0° C. More preferably, the first copolymer exhibits a glass transition temperature peak between about –50° C. and –10° C., and the second copolymer exhibits a glass transition temperature peak between about 12° C. and 65° C.

The presently preferred copolymers are prepared from silicone oligomers, butyl acrylate, methyl acrylate, methacrylic acid, acrylic acid, styrene, and an aliphatic urethane oligomer.

The addition of a urethane oligomer to the monomer mixture provides a number of benefits. First, it permits the copolymer to withstand higher cure temperatures such that the copolymer can be cured at a temperature that is more compatible with the cure temperatures for the rubber emulsions generally used for making formed rubber articles. This permits the copolymer coating and the rubber to be cured simultaneously. Second, a copolymer that includes a urethane oligomer can be used with a broader class of latexes and rubbers than a copolymer without a urethane oligomer. Specifically, such a copolymer can be used with natural rubber latex, either fresh or pre-cured, neoprene latex rubber or nitrile latex rubber. Fresh latex typically has a gel content in chloroform from 70 to 80%, while pre-cured latex has a higher gel content, typically from 80 to 90%.

For purposes of efficient emulsion polymerization, the copolymers of the present invention are produced as high solids content emulsions. However, high solids are not required for product coatings. Accordingly, the emulsions may be diluted to form a solids suspension containing from about 3 to 10% by weight, and preferably about 6% by weight of the total acrylic-based copolymer. Such a solids content is typical of those employed for mold coating and for depositing a coating on the surface of a formed rubber article.

For a release coating, the copolymer is preferably provided as an emulsion that includes a water-soluble, multivalent metal salt, which serves as a coagulant for the rubber emulsion. Preferably, a combined copolymer emulsion and coagulant emulsion is deposited directly on the mold for the rubber article to be formed. The object is to provide a surface concentration of coagulant salt that will enable coagulation of the latex onto the deposited copolymer coat in a commercially acceptable time. The preferred coagulant salt is calcium nitrate and is used in a concentration up to about 43%, preferably from about 20 to 40% by weight of the solids in the mixture.

While the copolymers prepared in accordance with the instant invention can be used for a variety of rubber article applications, including gloves, catheters, tubing, protective coverings, prophylactics, and the like, the primary focus of the disclosure is directed to their use in the manufacture of powder-free gloves. It will be appreciated that other rubber articles can be made by employing a wide variety of mold shapes and configurations.

In article manufacture, and in particular glove manufacture, a mold is coated with the copolymer emulsion and coagulant and then dried to form a copolymer and coagulant coating on the surface of the mold. The coated mold is then immersed into a rubber or latex emulsion from which the rubber deposits and coagulates onto the coated surface of the mold, forming a glove surface with an interior coating. The formed rubber article is then set, and a traditional leaching process is used to remove impurities from the formed article. Such impurities may include, for example, rubber compounding agents, accelerators, metal salts, and other compounds. At this point, if no further coatings are required, the formed article can be cured and stripped from the mold. However, if a second coating is to be applied, the formed article can either be cured and then coated with an optional second coating, or it can be coated and then cured.

If a second coating of a copolymer that is the same as or similar to the first copolymer coating is to be applied to the outer surface of the formed article, it is preferred that it be applied before curing. Doing so reduces the total number of steps involved in manufacturing the coated rubber article and saves energy, as an additional curing step is avoided. According to such a procedure, the partially set, formed article is immersed into an emulsion of the same or a different acrylic-based copolymer. While this surface is described as the outer surface for purposes of the manufacturing of a rubber article, the finished product will normally be turned inside out when stripped from the mold, such that the outer surface during manufacturing becomes the inner surface of the finished product. Therefore, for glove manufacture, the copolymer that is to be applied to the outer surface should provide a coating that exhibits good donning characteristics for the interior surface of the finished product. Once the second coat of copolymer is applied, the formed article is cured, cooled and stripped from the mold. This reverses the glove, placing the donning coat on the interior of the glove. It should be noted that the curing step will simultaneously cure the rubber as well as the coatings provided on the rubber.

While it is preferred to provide the second coating before curing, the rubber article can also be cured first and then coated with either a copolymer donning coating as described above, or some other coating. As necessary, a second curing step is provided and the formed article is cooled and stripped from the mold.

In the preferred embodiment, the same or a similar copolymer is used for both the donning and release surfaces of the product. For gloves, it is also preferred that the copolymer used for the donning coating also include a small amount of inert solids to provide an improved texture to the donning surface and prevent blocking. Examples of such inert solids include calcium carbonate, silicate or corn starch. Preferably, such solids are added to the copolymer in an amount of about 0.1% by weight solids. It should be noted that even though solids such as corn starch have been used for the donning coating in prior art gloves, the inclusion of such inert solids in the present invention is vastly different as such solids, rather than forming a dusty coating on the donning surface, are bound to the substrate by the copolymer. Consequently, even though gloves made using a donning coating of the present invention include inert solids, they are essentially "powder-free" as that term is used in the medical industry. As to gloves for use in clean room environment, the term "powder-free" is more narrowly defined. In order to make powder-free gloves for use in such a clean room environment, gloves using the coatings of the present invention must either be manufactured in a clean room environment, and/or rinsed in a clean room prior to use. However, even if rinsing is required, gloves using coatings of the present invention require far fewer rinsing steps than most prior art "powder-free" gloves.

In some embodiments, an improved feel for the donning surface can be achieved by the addition of a small amount of liquid to the copolymer donning coating. The inclusion of liquid provides an improved feel by acting as a skin moisturizer. Only a small amount of liquid is required, preferably in an amount of about 0.1% by weight solids.

The preferred copolymers have a surface friction that requires an average force of about 0.05 lb to less than about 0.3 lb, preferably about 0.2 to 0.25 lb, to move a sled weighing 200 g over the copolymer coated surface of the rubber article.

In practicing the present invention, the preferred mold is a contoured mold. While molds having a textured, to highly polished ceramic or porcelain surface, and molds having a fluorocarbon coating may be employed, it is preferred to employ a mold that is sufficiently textured to produce a matte finish in the deposited laminate formed by depositing the rubber from the latex onto the copolymer coating. This is achieved by roughening the mold surface by blasting with sand or glass beads. The preferred surfaces have been measured and shown to have a roughness of from about 8 to 10 microns, peak to valley.

Another advantage of the coatings of the present invention is that, at low temperatures, the coefficient of friction results in improved gripping. This property is useful for coated items such as gloves used as bacterial barriers in cold environments. For example, coated gloves of the present invention are useful for refrigerated and frozen food handlers such as butchers, meat packers, fishmongers and supermarket and kitchen employees. Such gloves may also be useful outdoors in cold temperatures such as might be encountered by emergency rescue, paramedic and police personnel.

DETAILED DESCRIPTION

Figure 1:
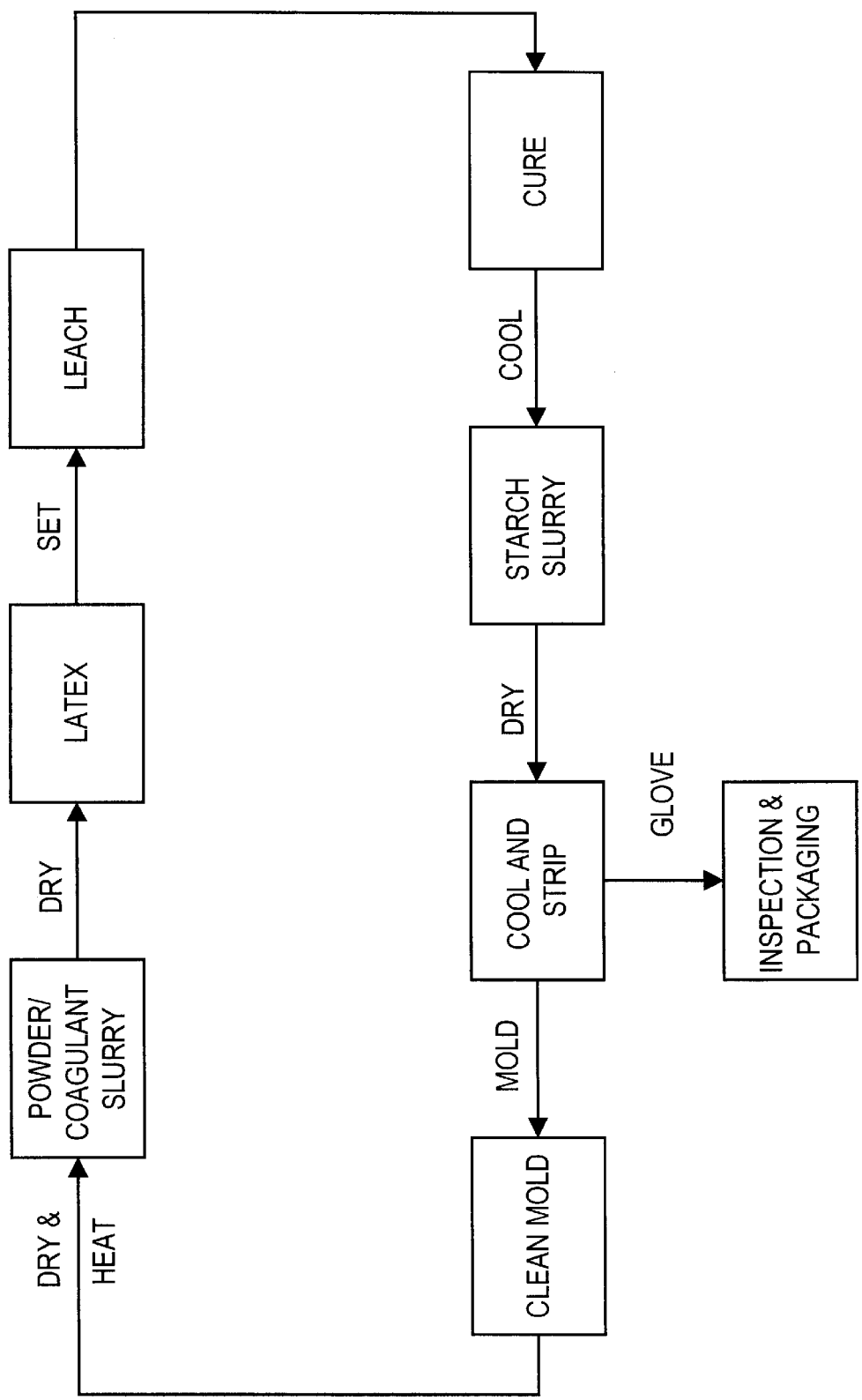
FIG. 1 is a flow diagram of the current method of rubber glove manufacture.

According to the present invention, non-tacky, acrylic-based copolymers are provided. The copolymers adhere aggressively to the surface of rubber articles and provide flexible coatings that can be stretched without separation from the rubber surface to which they are bonded. The copolymers are formed of at least one reactive low surface energy monomer, preferably one or more copolymerizable silicone oligomers; at least one alkyl acrylate; at least one aliphatic urethane oligomer; and at least one hard monomer.

The copolymers are useful for preparing powder-free coated rubber gloves that exhibit excellent mold-stripping and dry donning characteristics, and are also useful as protective coatings for other rubber articles.

As used herein, the term "rubber article" is meant to include articles formed from natural rubber or synthetic rubbers, including neoprene and nitrile rubbers. The latter yield premium articles. Such rubber articles are typically made by the coagulation of a latex emulsion onto a multivalent metal salt.

The term "low surface energy monomer" is used to refer to monomers which, if homopolymerized, would yield a polymer that requires only a low level of force to release the polymer from a surface to which it is applied. In the copolymers of the present invention, the copolymerizable low surface energy monomers reduce the energy required to release the copolymer coating from a surface, whether a mold, tissue or skin.

Nonlimiting examples of copolymerizable low surface energy monomers include copolymerizable silicones, fluorocarbons, fatty acid esters and the like, having alkenyl or vinyl, acrylic and/or methacrylic functionalities that facilitate copolymerization of the monomer. Copolymerizable silicone oligomers are preferred.

The term "copolymerizable silicone oligomer," as used herein, refers to polymeric siloxanes and silicones having acrylate, methacrylate or vinyl functionalities, including but not limited to acrylated polysiloxanes. The acrylate, methacrylate or alkenyl or vinyl functionality is at least 1, preferably from about 2 to 3.

Examples of the copolymerizable silicone oligomers include the Tegot Silicone acrylates RC 149, 300, 450, 710, 720 and 802 and ZMR1395 manufactured and sold by Goldschmidt Chemical Corporation (Hopewell, Va.). They are linear polydimethylsiloxanes with multiacrylate functionality and a molecular weight between about 1,000 and 20,000 g/mol. They include the reaction product of polydimethylsiloxanes and pentaerythritoltriacrylate. They also include silicone systems such as GE 6000, a vinyl polydimethyl siloxane, and 6010 catalyst concentrate, manufactured and sold by GE Silicones division of General Electric Company.

The copolymerizable low surface energy monomers are employed in a concentration of from about 0.7 to 20%, preferably about 1 to 15% by weight, based on the total weight of monomers forming the acrylic-based copolymer. They impart improved dry donning characteristics, as well as improved mold release characteristics, to the copolymer coating.

The aliphatic urethane oligomers are employed in a positive amount, up to about 10% by weight, based on the total weight of monomers forming the copolymer. Preferably, the urethane oligomers are added in an amount between about 3 and about 5% by weight with a most preferred amount being about 3.8% by weight. The addition of a urethane oligomer allows the copolymer to tolerate higher cure temperature, and also allows the use of high concentrations of coagulants without causing the formed article to stick to the mold. The addition of a urethane oligomer is especially useful for coating articles made from either precured or fresh natural latex. However, the inclusion of too much urethane oligomer can adversely affect the bond between the coating and substrate, and thereby cause flaking of the coating from the subgtrate surface.

The preferred aliphatic urethane is a product known as Ebecryl 270, made by Radcure (Smyrna, Ga.), a business unit of UCB Chemicals (Brussels, Belgium). Ebecryl 270 is a UV-reactive aliphatic urethane diacrylate prepolymer based on an acrylated aliphatic isocyanate. Its weight average molecular weight ($M_w$) is believed to be about 1500 and its viscosity is about 2700 centipoise at 60° C. As a film, it has good flexibility with a tensile strength of about 1000 psi and a tensile elongation of about 60%. It is also UV resistant such that articles coated with a coating that includes Ebecryl 270 are lightfast. The inclusion of an aliphatic urethane oligomer such as Ebecryl 270 also yields a matte or low gloss finish to the coated articles. Low gloss is important in that it prevents blocking of the finished articles.

The balance of the monomers are selected to provide good bonding to a latex surface, good donning characteristics, a good tactile feel, and good mold release properties. One class of monomers used in forming the copolymers are alkyl acrylate monomers containing from 1 to about 10 carbon atoms in the alkyl group. These monomers are present in a total amount of from about 30 to 80% by weight of the monomers, preferably from about 40 to 80% by weight, based on the total weight of monomers forming the acrylic-based copolymers. Nonlimiting examples of such alkyl acrylate monomers include methyl acrylate, ethyl acrylate, butyl acrylate, propyl acrylate, 2-ethylhexyl acrylate, isooctyl acrylate, isodecyl acrylate, and the like. The presently preferred alkyl acrylate monomers are butyl acrylate and methyl acrylate.

In addition to silicone oligomers, alkyl acrylates, and urethane oligomers, the monomer mixture further comprises a balance of hard monomers. As used herein, "hard monomers" are monomers which, if homopolymerized, yield a polymer having a glass transition temperature ($T_g$) greater than about 25° C. Nonlimiting examples include styrenic monomers, such a styrene, alpha-methyl styrene, vinyl toluene, and the like; alkyl methacrylates, such as methyl methacrylate, ethyl methacrylate, butyl methacrylate and the like; and amides, such as an n-isobutoxymethyl acrylamide and the like. Hard monomer content is from about 20 to 60% by weight, based on the total weight of monomers forming the acrylic-based copolymer.

The monomer mixture used to form the copolymer also preferably includes one or more unsaturated carboxylic acids containing from 3 to about 5 carbon atoms. Nonlimiting examples are acrylic acid, methacrylic acid, itaconic acid and the like. The carboxylic acids improve the cohesive strength of the resulting polymer and promote polymer adhesion to rubber and other surfaces, and are pregett in a concentration of from about 1 to 6% by weight, preferably from about 2 to 6% by weight of the copolymer emulsion.

Other vinyl unsaturated monomers that aggressively copolymerize with the principal monomers of the invention and do not create a residual monomer contamination problem may also be used to modify polymer properties. Nonlimiting examples include one or more vinyl esters containing from 2 to about 16 carbon atoms in the alkyl group of the acid. Representative vinyl esters include Yinyl acetate, vinyl butyrate, vinyl propionate, vinyl isobutyrate, vinyl valerate, vinyl versitate, and the like.

Other useful monomers include diesters of dicarboxylic acids and mixtures thereof, in which each ester group of the diester independently contains from about 8 to 16, preferably from about 8 to 12, carbon atoms. The preferred diesters are di-2-ethylhexyl maleate (dioctyl maleate), di-2-ethylhexyl furmarate, and mixtures thereof.

The monomers are selected to provide sufficient elongation so that the acrylic-based copolymer coating will stretch or elongate with the rubber with minimal cracking, flaking or debonding. Suitable copolymers have an elongation of 100 to 500% or more, typically from about 100 to 300% when self bonded to a rubber surface.

In one embodiment of the invention, the emulsion copolymers are prepared by sequential polymerization of at least two monomer mixtures and yield at least two distinct copolymers, one of which has a glass transition temperature below about 0° C., more preferably, between about −50° C. and −10° C., and the other copolymer has a glass transition temperature above about 0° C., more preferably about 12° C. to 65° C. Solids contents ranges from about 40 to 70% by weight of the total composition. Polymerization is preferably carried out in the presence of free radical catalysts and one or more surfactants, with the surfactant system being present in an amount of from about 0.5 to 5 parts by weight surfactant per 100 parts by weight monomers, preferably, about 3 parts surfactant per 100 parts monomers.

The presently preferred surfactant system is a combination of anionic surfactants. Nonlimiting examples include sodium dialkyl sulfosuccinates, salts of sulfated alkyl phenoxypoly (ethyleneoxy) ethanol, and sodium lauryl ether sulfate. The presently preferred surfactant system is one employing 37.4% by weight of the ammonia salt of sulfated nonylphenoxypoly (ethyleneoxy) ethanol, 21.8% by weight of sodium dioctyl sulfosuccinate, and 40.8% by weight of sodium lauryl ether sulfate. The combination of anionic surfactants enables the formation of a stable suspension of the acrylic-based copolymers of the invention.

Polymerization catalysts that are useful in initiating the polymerization reactions include water-soluble free-radical initiators, for example, persulfates, such as sodium persulfate and potassium persulfate; peroxides, such as tertiary-butyl hydroperoxide and the like. Such catalysts are used alone or in combination with reducing agents or redox catalysts such as sodium meta-bisulfite and the like. The catalysts should be present in an amount of from about 0.15 to 0.5 parts by weight per 100 parts by weight of the monomers, with surfactants present in an amount of from about 0.5 to 5% by weight, based on the weight of the monomers. Reaction temperature generally ranges from about 65 to 85° C.

The monomer mixture used to form the copolymers of the present invention may also include chain transfer agents, for example, organic compounds containing mono- or multi-mercaptan groups, chlorinated groups, hydroxy groups, or the like, as are known in the art. Such chain transfer agents are useful for controlling the average polymer chain length of the acrylic-based copolymers. The presently preferred chain transfer agents are n-dodecyl mercaptan and t-dodecyl mercaptan, provided in a concentration from about 0.01 to 0.1% by weight of the monomers. In addition, internal crosslinking may be induced by the use of multifunctional acrylates and methacrylates.

Figure 2:
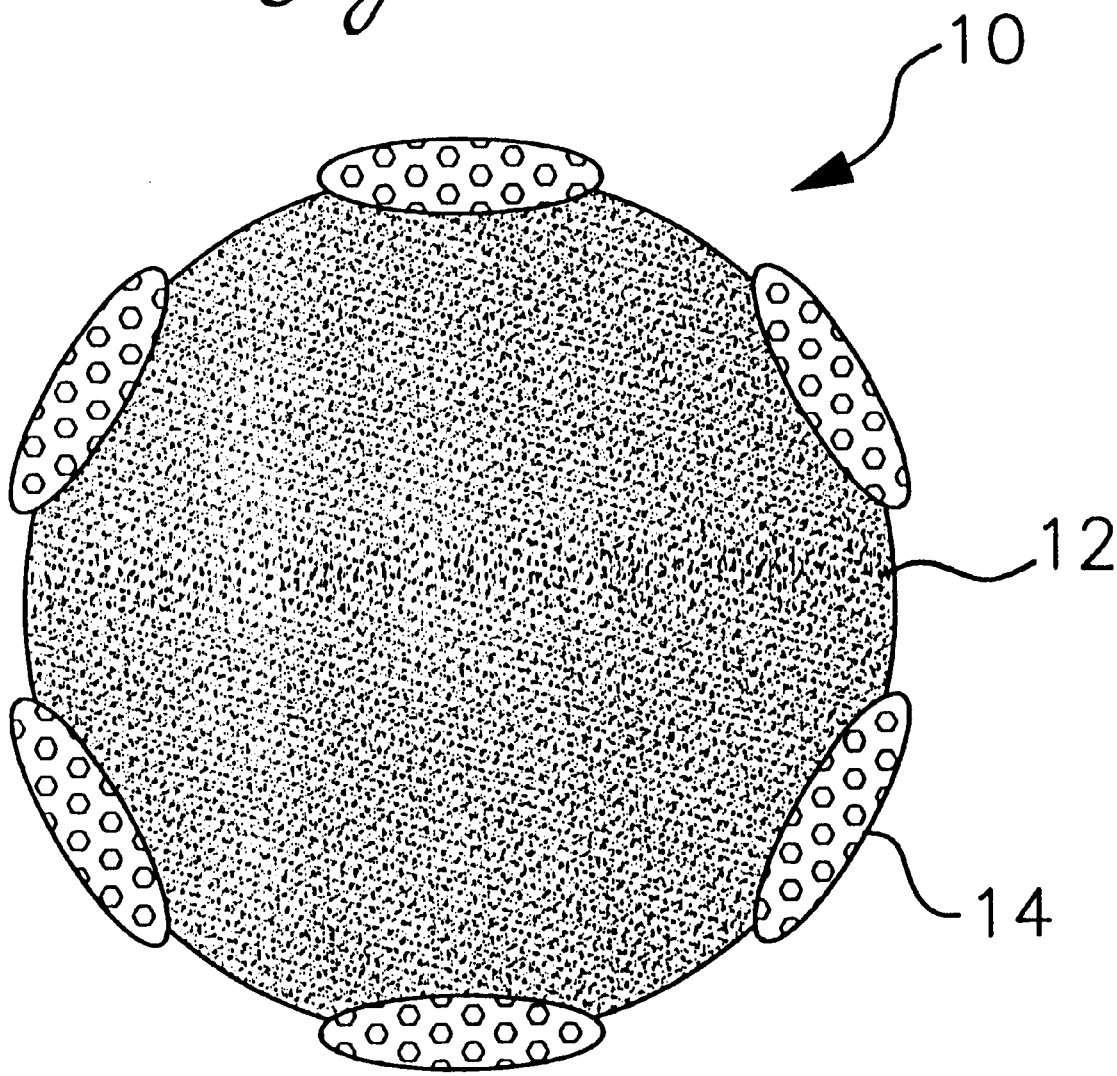
FIG. 2 is a depiction of a sequentially polymerized polymer particle.
Figure 3:
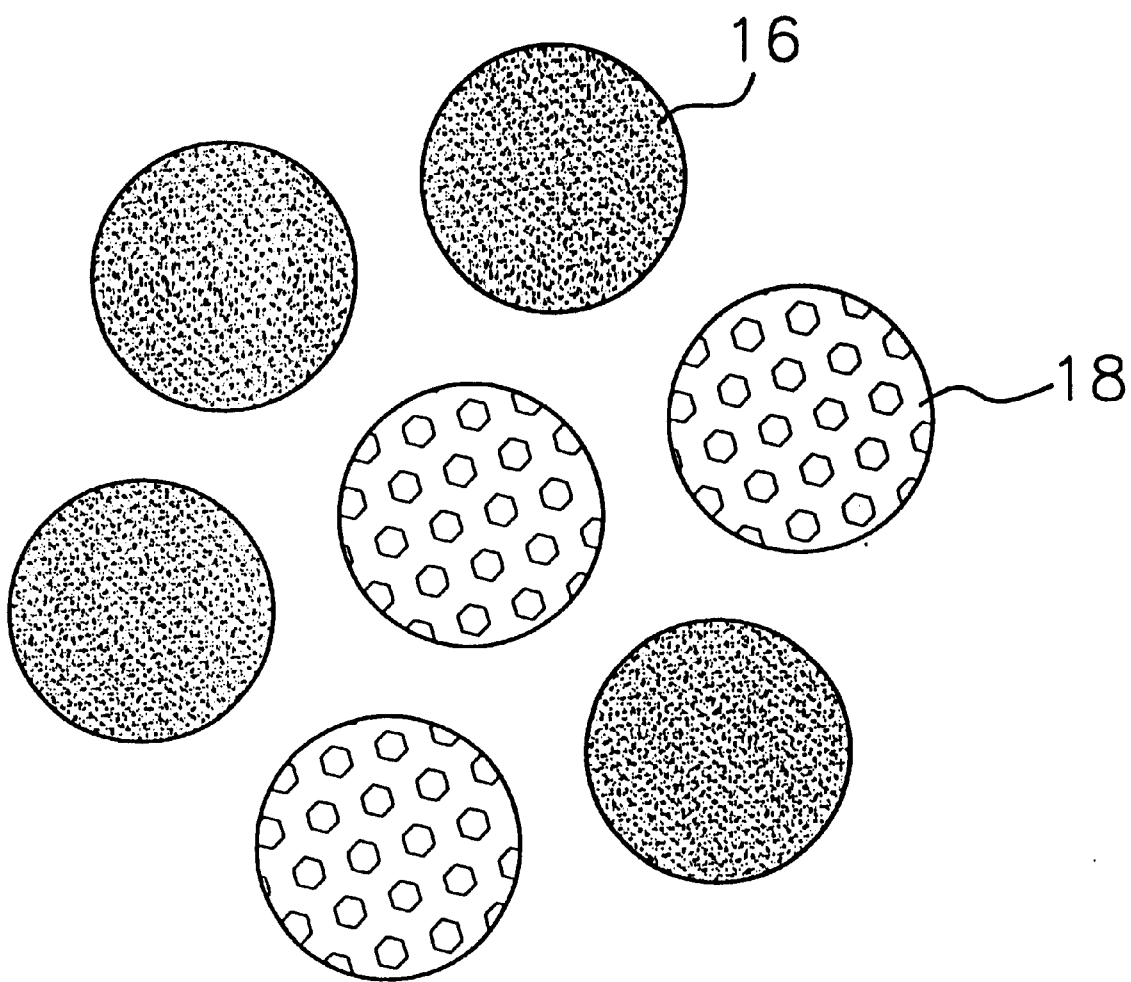
FIG. 3 is a depiction of a mixture of separately polymerized polymer particles.

Polymerization is carried out by preparing a pre-emulsion mixture of monomers and commencing polymerization using free-radical initiators. The monomer mixture can be introduced into the reactor as a single charge, or fed in incrementally to control the rate of reaction. Preferably, a sequential polymerization is used whereby the monomers are emulsified and allowed to react in distinct stages. In the preferred embodiment, two different monomer mixtures are provided and sequentially and gradually fed into the reactor. For the first monomer mixture, polymerization is initiated and allowed to propagate while the monomer mixture is gradually fed into the reactor. After polymerization of the first monomer mixture, a second monomer mixture is gradually fed into the reactor and polymerization continues. The result is a copolymer system of emulsified copolymer particles distinct from emulsion copolymers prepared by batch polymerization. Although not bound by theory, it is believed that sequential polymerization of the two monomer mixtures results in an emulsion of domain-type copolymeric particles, each having an inner core of first copolymeric composition and an outer shell or region of second copolymeric composition, partially or totally encapsulating the core. Such a copolymer system is illustrated in FIG. 2, which is a depiction of a sequentially polymerized polymer particle. According to this figure, a sequentially polymerized polymer particle 10 is comprised of a central core 12 formed from the copolymerization of the first monomer mixture. The centra core is either completely, or, as shown, partially surrounded by a second polymerized outer shell 14 produced by the copolymerization of the second monomer mixture. In contrast, and as depicted in FIG. 3, if the individual monomer mixtures are separately copolymerized and then blended together, they form a random mixture of copolymer particles 16 formed from the first monomer mixture and copolymer particles 18 formed form the second monomer mixture. As shown, there is little or no attachment or association between the different copolymer particles.

Of the rubber articles that can be manufactured in accordance with this invention, examination and surgical gloves have the most critical requirements. Because of their complex shape, they must be capable of being stripped from a mold using commercially acceptable practices and yet, when stripped from the mold, yield a surface having good tactile feel; that is, enable someone wearing the gloves to pick up articles with a good grip. In this regard, good tactile feel is generally contrary to good mold stripping. However, the use of a copolymer according to the instant invention results in a coated article with both good mold stripping and good tactile feel properties. The roughness of the tactile surface of a glove can be further improved by using a mold that has been roughened, such as by blasting with sand or glass beads, to provide a desired tactile surface to the glove. Preferred roughened surfaces have a roughness of about 8 to 10 microns peak to valley. Other textures may also be used. In addition to improving the tactile feel, a rough outer surface of the glove or other article helps to prevent blocking when several articles are stacked atop one another.

While good mold stripping characteristics as well as good tactile feel are desired for coating a fist side of the glove, the opposed or inner surface of the glove must enable good (dry and/or wet) donning, that is, the ability to be stretched and slid over the surface of skin, whether wet or dry, without excessive resistance. As with the outer surface, it is also preferred that the donning surface be rough. In addition to improving the glove's donning properties, a rough inner surface also helps to prevent internal blocking of glove. While the smoothness of the tactile surface can be controlled by the mold surface, the smoothness of the donning surface is generally dictated by the physical properties of the coating applied over the latex. However, as pointed out above, the inclusion of a urethane oligomer such as Ebecryl 270 in the monomer mix can help provide a desirable low gloss surface to the finished article.

Figure 4:
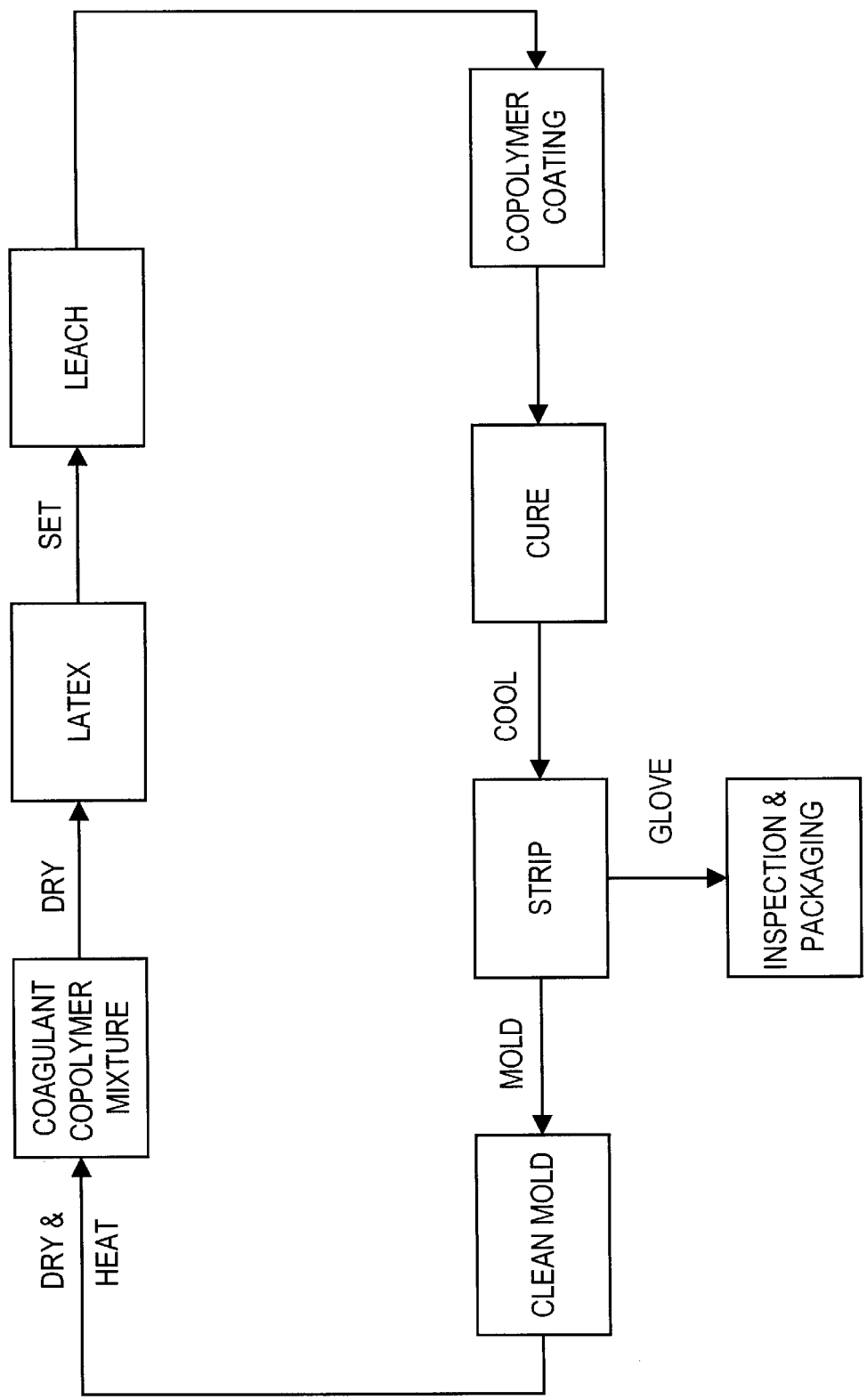
FIGS. 4 and 5 are flow diagrams of methods for manufacturing rubber gloves using copolymer coatings of to the present invention.
Figure 5:
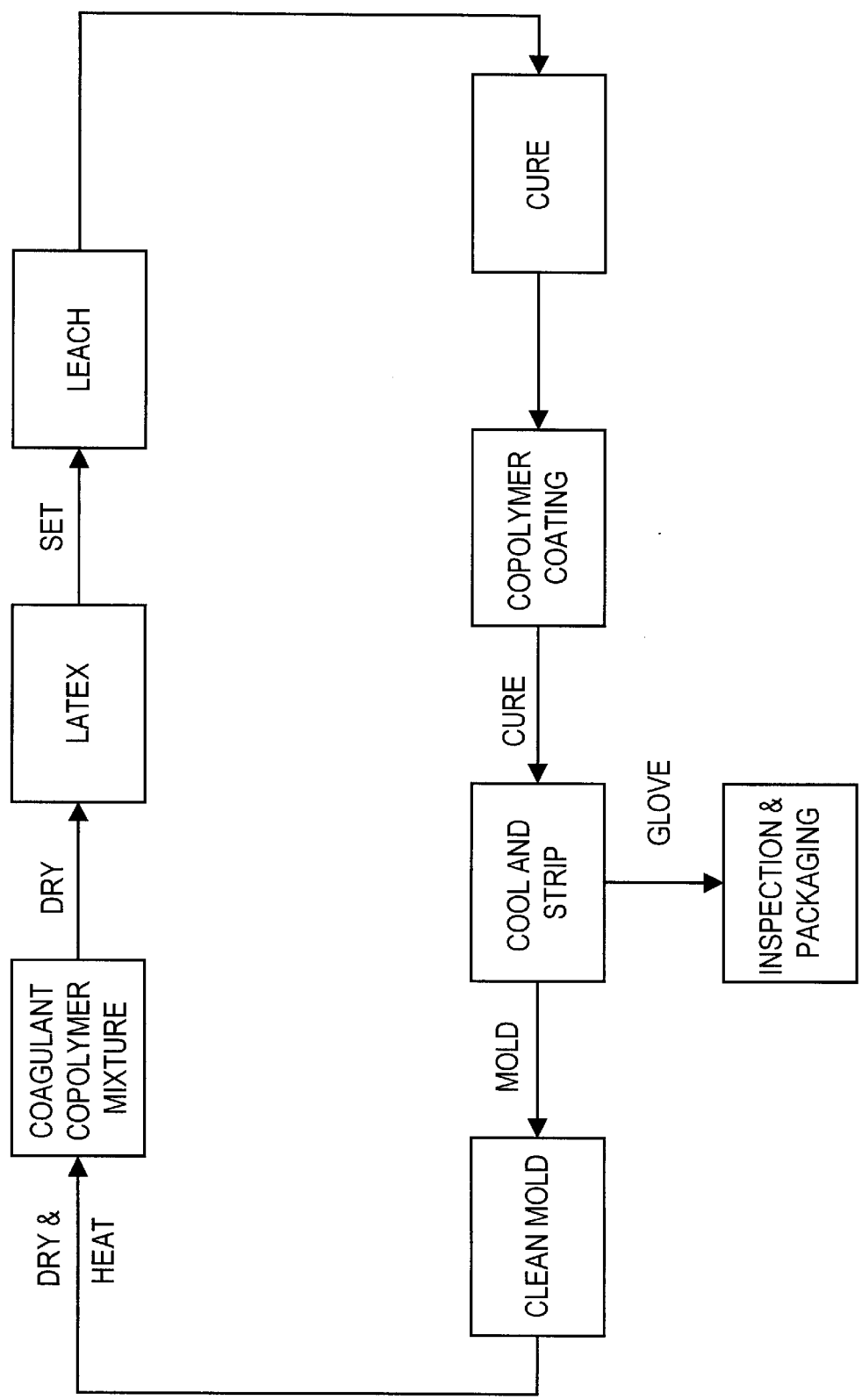

With reference to FIGS. 4 and 5, two processes for producing a powder-free glove using the coatings of the present invention are shown. Under either process, first, a mold in a contoured shape of a hand is coated with an acrylic-based copolymer emulsion of this invention which exhibits good mold release and stripping properties. The copolymer coating is preferably provided as an emulsion that includes a coagulant. The copolymer coating step is preferably performed by dipping a mold into a bath of the combined copolymer and coagulant emulsion at a temperature of between about 25 and 60° C. It should be noted that such a temperature is useful for preheating the mold prior to the application of the latex emulsion, but not an essential step. As an alternative, the copolymer and coagulant emulsion can be applied at room temperature and then the mold can be heated prior to forming the latex substrate. It should also be noted that if a nitrile latex rubber glove is to be formed, the mold is dipped in a coagulant that contains none of the copolymer of the present invention as good mold release properties can be attained without the inclusion of the copolymer. Once the mold is sufficiently coated with either the coagulant or coagulant and copolymer emulsion, generally after less than about five seconds, the coated mold is removed from the emulsion and dried at a temperature between about 100 and 130° C.

A rubber glove is then formed over the coated mold by deposition of a rubber latex slurry onto the coated mold. The rubber latex coagulates onto the surface of the mold, providing shape to the rubber article. Preferably, the rubber latex is deposited on the coated mold by dipping the coated mold into a bath containing a latex emulsion at room temperature for a period of time sufficient to provide a glove of the desired thickness based on the type and concentration of rubber latex emulsion being used. One important benefit of the copolymer coating of the present invention is that it is able to tolerate high levels of coagulant without causing sticking of the article to the mold. This is especially useful in the manufacture of neoprene latex rubber gloves which tend to be thicker, and therefore, require higher amounts of coagulant than other types of latex gloves, The rubber glove is then heated to a temperature between about 80 and 110° C. for a short period of time to set the rubber. Following the setting step, the rubber glove is leached in a water bath at about 45 to 65° C. to leach the water soluble impurities from the formed article.

Following leaching, in one embodiment of the invention, as illustrated in FIG. 4, the rubber glove is dipped in a second acrylic-based copolymer emulsion according to the present invention. Unlike the first copolymer emulsion, this emulsion contains no coagulating electrolyte. The second copolymer emulsion is preferably applied at room temperature. The formed rubber article is held in this emulsion for a short period of time and is then removed from the second copolymer emulsion and cured at a temperature of between about 80 and 135° C. for about 15 to 30 minutes. The curing process simultaneously cures the rubber as well as drying and/or curing the first and second coatings. The cured and coated glove is then cooled and stripped from the mold.

According to a second embodiment as illustrated in FIG. 5, the rubber glove is cured after the leaching step and before a second copolymer coating is applied. According to this embodiment, after leaching, the rubber glove is cured in a curing oven at between about 80 and 135° C. for between about 15 and 30 minutes. A second acrylic-based copolymer emulsion is then applied. This is done by dipping the cured rubber glove in the second copolymer emulsion at a temperature of between about 100 and 120° C. for a short period of time. This outer coating of copolymer is then air dried at room temperature. The cooled glove is then stripped from the mold. Of course, rather than applying a second copolymer emulsion of the present invention, a conventional powder coating could alternatively be applied.

In either embodiment, once the glove has been stripped from the mold, the mold is reused. For gloves made of nitrile latex rubber or natural rubber latex, the mold is then cleaned and rinsed, dried, and preheated at a temperature between about 45 and 70° C. The preheated mold is then recycled such that the process described above is repeated to make additional gloves. For gloves made of neoprene, several cycles can be completed before cleaning is necessary. Up to 25 or more cycles can be completed before cleaning is necessary, and then, cleaning requires just soap and water. This is a vast improvement over prior art release coatings where after five to ten cycles, cleaning with strong solvents was required.

It should be recognized that the step of the current invention where a copolymer coating is applied to a mold for transfer to a latex rubber replaces the prior art step of depositing a coagulant slurry to the mold surface. Similarly, the step of depositing the copolymer on a formed article replaces the step of coating the article with a starch slurry or some other donning coating. Therefore, for ease of manufacture, the presently preferred embodiment is that of FIG. 5 as very little, if any, modifications are required to the manufacturing line. However, because the simultaneous curing of the latex rubber substrate and the copolymer coatings improves the bond between the substrate and the coating, for improved product performance, the embodiment of FIG. 4 is preferred.

Coating both the inner and outer surfaces of the glove with an acrylic-based copolymer according to the present invention yields a glove having excellent donning properties as well as an improved tactile surface. Since stripping turns the glove inside out, the donning surface is formed on the outside surface during manufacture but is reversed by the mold stripping step. In the preferred embodiment for natural rubber latex and neoprene rubber latex articles, both the donning and tactile surfaces are coated with an acrylic-based copolymer of the present invention. However, for nitrile latex rubber gloves, just a copolymer donning coating is applied. In other situations it may be desired to use the preferred copolymer on only one surface, either the donning or the release surface. If the copolymer is just to be used for the donning surface, then similar to the production of nitrile latex rubber articles, some other coating, or merely a coagulant slurry, can replace the first step. A donning copolymer coating according to the present invention can then be applied to the outer surface of the formed rubber article as set forth above. Similarly, in other embodiments, it may be desired to only include the copolymer of the present invention as a release coating. For such embodiments, some other donning coating can be applied, or perhaps, the donning coating can be omitted entirely.

The thickness of the formed rubber article is generally determined by the concentration of the latex rubber emulsion as well as the amount of time that the mold is immersed in the latex rubber emulsion. A typical thickness for natural or nitrile latex rubber articles is from about 150 to 250 microns. Neoprene latex rubber articles are generally thicker, up to about 760 microns. The coatings of the present invention are preferably applied to form dried thicknesses of between about 3 and 10 microns.

The emulsion coating copolymers of this invention can be used alone or in combination with inert granular solids such as calcium carbonate, silicate, starch, or the like, in order further to enhance the donning characteristics of the finished product. It is presently preferred to include corn starch in the copolymer an amount of about 0.1% total weight of the copolymer emulsion. A suitable corn starch is 400 L-NF corn starch made by Roquetle America, Inc., Keokuk, Iowa. The donning coat can also include a small amount, about 0.1% total weight of the copolymer emulsion, of a moisturizing liquid such as octyl isononanoate or Neobee M-20, a polyol diester of a short chain fatty acid manufactured by Stepan Chemical Co., Northfield, Ill.

As pointed out above, for coatings having good donning and stripping properties, the copolymer coatings are preferably formed by sequential polymerization. Preferably, the first copolymer pre-emulsion has a low glass transition temperature, and the other a copolymer has a high glass transition temperature. The two, in combination, provide a non-tacky copolymer composition having at least one significant glass transition temperature of about 15° C. or more, and preferably about 15 to 60° C.

Figure 6:
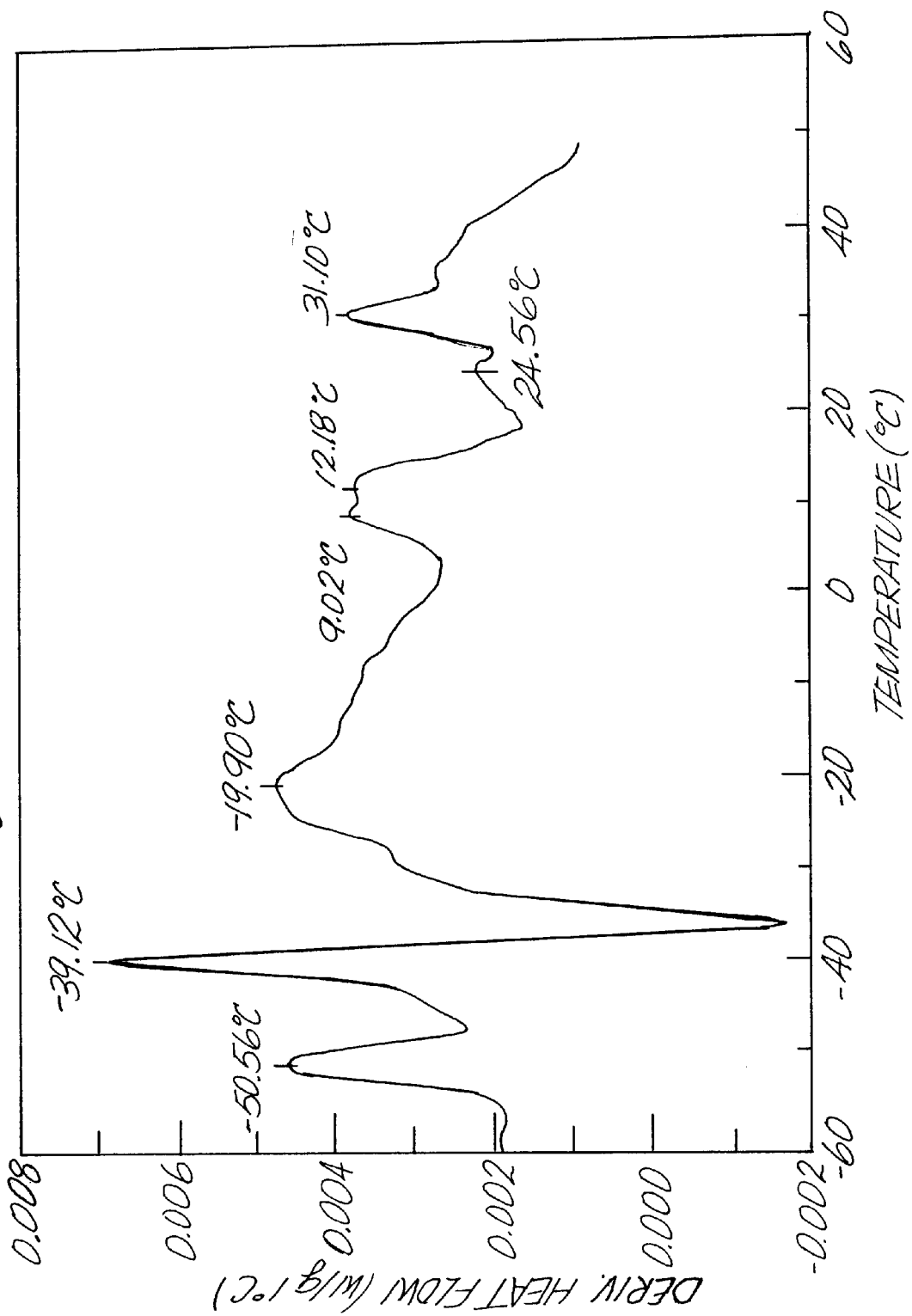
FIG. 6 is a Differential Scanning Calorimetry (DSC) plot of the derivative of heat flow as a function of temperature, showing glass transition temperature peaks for the preferred copolymer coating of the invention.

In particular, FIG. 6 is a plot of glass transition temperature of a sequentially polymerized mixture of copolymers with a major glass transition temperature peak below 0° C. and a minor glass transition temperature peak above 0° C. for use as a copolymer coating. While, not bound by theory, in this "core and shell" approach to sequential polymerization of two monomer systems, it is believed there is formed a continuous phase of the low glass transition temperature copolymer having dispersed therein or thereon, the high glass transition temperature copolymer as depicted in FIGS. 2 and 3.

For good mold release characteristics, it is presently preferred that the copolymer composition used for the mold release coating has a weight ratio of low glass transition temperature copolymer to high glass transition temperature copolymer of from about 1:1 to 1:3, more preferably from about 1:1 to 1.5:1.

For good donning characteristics, it is presently preferred that the copolymer composition used for the donning coating has a weight ratio of low to high glass transition temperature copolymers of about 3:1 to 1: 1, more preferably about 1.2:1 to 1:1.

It has been observed that, if too much high $T_g$ copolymer is present, flaking will occur. In addition, for good dry donning, it is desirable that the copolymer form as domains or micro articles. This provides in essence, a rough surface, which is desirable for good donning. If too much low glass transition temperature copolymer is employed, there can be blocking problems with the formed articles.

It is also desirable that the copolymer emulsion tolerate coagulants typically employed for latex coagulation, in concentrations typically used for latex coagulation. The typical electrolyte concentration is in the range of up to about 43% by weight of suspension.

The copolymers of this invention can be prepared to provide both a high cohesive strength and holding power to natural and synthetic rubber surfaces, as well as the ability to stretch with the rubber surfaces and enable donning. The copolymers generally exhibit a mean coefficient of friction from about 0.05 to 0.3 lb, typically from about 0.2 to 0.25 lb. The preferred copolymer coating thickness is from about 10 to 25 microns, preferably from about 12 to 16 microns.

The inclusion of multifunctional monomers such as tetramethylpropane triacrylate and the like, which undergo crosslinking reactions, and chain transfer agents as part of the monomer mixture results in the formation of internally crosslinked emulsion polymers. This differs from externally crosslinked polymers in that the functional groups, such as carboxyl, hydroxyl, and/or amino groups, remain free and available for improving bonding and are available for external crosslinking reactions such as by exposure to actinic, electron beam radiation and/or through external crosslinking agents.

The copolymers can be used as such or modified by the addition of vinyl-addition silicone polymers present in an amount up to about 30% by weight based on the weight of the monomer mixture and vinyl-addition silicone system. The preferred vinyl-addition silicone systems comprise silicone monomers having alkenyl or vinyl unsaturation, mixed with silicone hydride crosslinkers. Such systems are cured using a Group VIII metal catalyst, preferably a platinum catalyst.

The copolymers of this invention are formed to high solids content during emulsion polymerization, making the emulsion polymerization process more efficient. They are normally diluted to form a suspension having a lower solids content, which facilitates coating of the composition on a mold used to form the rubber article, or onto the formed rubber article itself. As is known in the art, typical solids content ranges from about 3 to 10% by weight of the suspension.

A coagulant salt is required to cause the rubber to deposit from its emulsion (latex) onto a surface of the polymer. The coagulant can be applied after drying of the copolymer on the surface of the mold, however, a considerable savings in time and cost can be realized by combining a coagulant with the copolymer suspension. It has surprisingly been found that the copolymer suspensions of the instant invention can tolerate the high amount of polyvalent metal salts that serve as a coagulant if the multi-component anionic surfactant system is employed. Examples of coagulants that can be used are water soluble salts of calcium, zinc, aluminum and the like. Calcium nitrate is presently preferred. A coagulant salt, preferably calcium nitrate, is normally provided in a concentration of up to about 43% by weight of the suspension, typically from about 20 to 40% by weight of suspension, for mold coating. Combining the coagulant with the emulsion polymers of the instant invention eliminates a significant step in the production of copolymer coated rubber articles. If the copolymer is applied without coagulant, then the coagulant must be applied to the surface of the copolymer after the copolymer has been deposited and dried on the surface of the mold. This adds a step and is, therefore, a more expensive measure.

It has also been discovered that for some applications, the coating's adherence to the substrate can be improved if a first copolymer as set forth above is blended with a second copolymer produced from the reaction of a monomer mix that does not include a urethane a oligomer. Examples of such copolymers that do not include a urethane oligomer are set forth in detail in application Ser. No. 08/878,144, filed Jun. 18, 1997, and Ser. No. 08/389,571, filed Feb. 14, 1995, both of which have already been incorporated by reference.

The presently preferred molds are smooth contoured molds having a textured, or smooth ceramic, porcelain or a fluorocarbon surface that will accept the coating of the copolymer, or the copolymer and coagulant, and release the formed rubber article at the completion of the process.

While the focus of the discussion has been directed to copolymer coatings for rubber articles and in particular gloves, the copolymers of the present invention are meant to be employed in a wide range of applications, including providing "soft touch" products for use in the automobile industry. One example is in providing polymeric laminates having a leather look with a feel to match.

The copolymers of this invention are also meant to be used in vacuum formable laminates. The product construction would consist of a polyester film acting as a carrier, which is removed prior to vacuum forming. The copolymers of the instant invention are deposited on the carrier at about 0.25 to 2 mils in thickness, to act as a clear or pigmented top coat and as the surface that is felt by the user. The balance of the construction consists of material deposited to give the appearance of leather, wood grain or the like, as the layer of the copolymer of the instant invention adds or insures the "soft touch". There is then added a layer of heat activated adhesive, followed by heat and pressure bonding to a 20 mil sheet of polymeric material compatible with the injection molding plastic. The polyester carrier is then removed and the laminate is vacuum formed and insert molded to give a contoured plastic part with a unique and desirable soft feel.

The copolymers of the instant invention are also meant to be used as a spray coating and can be used in producing waterproof fabrics, mold release agents or abrasion resistant coatings. Films of the copolymers of the present invention could also be formed by deposition on a backing having a pressure-sensitive adhesive on the opposite side. The copolymers provide protective and unusual "soft touch" performance properties. In either application, the polymer is believed to have unusual exterior performance properties due to containing silicone and acrylic monomers. Coatings of this type will provide excellent U.V. resistance.

The invention is described in further detail by reference to the following examples.

EXAMPLES 1–4

Emulsion Copolymer Production.

First and second Soap Solutions, Monomer Mixtures and Catalyst/Activator mixtures were prepared for each of Examples 1 to 4 as set forth in Table 1. The parentheticals (1) and (2) denote separate changes of ingredients used in the sequential polymerization process.

TABLE I

PREPARATION OF PRE-EMULSION MONOMER MIXTURES

| | EXAMPLE 1 (grams) | | EXAMPLE 2 (grams) | | EXAMPLE 3 (grams) | | EXAMPLE 4 (grams) | |
|---|---|---|---|---|---|---|---|---|
| | (1) | (2) | (1) | (2) | (1) | (2) | (1) | (2) |
| Soap Solution | | | | | | | | |
| deionized water | 90.56 | 76.09 | 91.24 | 76.17 | 90.56 | 76.09 | 90.56 | 76.09 |
| tetrasodium pyrophosphate | 0.79 | 0.66 | 0.74 | 0.61 | 0.79 | 0.66 | 0.79 | 0.66 |
| Aerosol ™ NPES 458 | 9.57 | 8.03 | 9.57 | 7.98 | 9.57 | 8.03 | 9.57 | 8.03 |
| Aerosol ™ OT 75 | 4.43 | 3.72 | 4.42 | 3.68 | 4.43 | 3.72 | 4.43 | 3.72 |
| Disponil FES 77 | 19.65 | 16.50 | 19.43 | 16.21 | 19.65 | 16.50 | 19.65 | 16.50 |
| Total | 125.00 | 105.00 | 125.40 | 104.60 | 125.00 | 105.00 | 125.00 | 105.00 |

TABLE I-continued

PREPARATION OF PRE-EMULSION MONOMER MIXTURES

| | EXAMPLE 1 (grams) | | EXAMPLE 2 (grams) | | EXAMPLE 3 (grams) | | EXAMPLE 4 (grams) | |
|---|---|---|---|---|---|---|---|---|
| | (1) | (2) | (1) | (2) | (1) | (2) | (1) | (2) |
| Monomer Mix | | | | | | | | |
| styrene | 33.60 | 147.20 | 33.60 | 146.60 | 33.60 | 149.30 | 34.80 | 149.30 |
| butyl acrylate | 257.80 | 88.80 | 257.80 | 81.40 | 257.80 | 88.80 | 257.80 | 88.80 |
| methyl acrylate | 42.40 | 37.80 | 44.40 | 39.40 | 42.40 | 37.80 | 42.40 | 37.80 |
| methacrylic acid | 4.30 | 4.10 | 4.30 | 5.30 | 4.30 | 4.70 | 4.30 | 5.20 |
| acrylic acid | 4.60 | 3.70 | 4.60 | 4.70 | 4.60 | 4.20 | 4.60 | 4.70 |
| RC 726 | 23.40 | — | 23.40 | — | 23.40 | — | 23.40 | — |
| SL-6000-D1 | 30.40 | 47.20 | 30.40 | 47.20 | 30.40 | 47.60 | 30.40 | 47.60 |
| SL-6010-D1 | 19.90 | — | 20.00 | — | 19.90 | — | 20.00 | — |
| Ebecryl 270 | 10.34 | 25.40 | 10.90 | 23.90 | 12.40 | 26.60 | 12.40 | 27.10 |
| Total | 426.74 | 354.20 | 429.40 | 356.50 | 428.80 | 359.00 | 430.10 | 360.50 |
| Catalyst/Activator | | | | | | | | |
| deionized water | 62.80 | 63.50 | 62.80 | 63.50 | 62.80 | 61.15 | 62.80 | 61.50 |
| potassium persulfate | 2.20 | — | 2.20 | — | 2.20 | — | 2.20 | — |
| sodium metabisulfite | — | 1.50 | — | 1.50 | — | 3.85 | — | 3.50 |
| Total | 65.00 | 65.00 | 65.00 | 65.00 | 65.00 | 65.00 | 65.00 | 65.00 |

Initial Reactor Charges and Rinse Solutions were prepared for each of Examples 1 to 4 as set forth in Table II:

TABLE II

PREPARATION OF INITIAL REACTOR CHARGES AND RINSE SOLUTIONS

| | EXAMPLE 1 (grams) | EXAMPLE 2 (grams) | EXAMPLE 3 (grams) | EXAMPLE 4 (grams) |
|---|---|---|---|---|
| Initial Reactor Charge | | | | |
| deionized water | 317.05 | 317.05 | 317.05 | 317.05 |
| Aerosol ™ NPES 458 | 2.00 | 2.00 | 2.00 | 2.00 |
| sodium bicarbonate | 4.00 | 4.00 | 4.00 | 4.00 |
| potassium persulfate | 1.80 | 1.80 | 1.80 | 1.80 |
| sodium metabisulfate | 0.15 | 0.15 | 0.15 | 0.15 |
| Total | 325.00 | 325.00 | 325.00 | 325.00 |
| Rinse Solution | | | | |
| deionized water | 27.06 | 21.10 | 19.20 | 22.40 |
| ammonia (28%) | 6.00 | 6.00 | 6.00 | 6.00 |
| Drewplus L-191 | 1.00 | 1.00 | 1.00 | 1.00 |
| Kathon LX | 1.00 | 1.00 | 1.00 | 1.00 |
| Total | 35.06 | 29.10 | 27.20 | 30.40 |

For Example 1, first and second pre-emulsion monomer mixtures were prepared by combining the first Soap Solution with the first Monomer Mix and the second Soap Solution with the second Monomer Mix. As explained above, the Soap Solution includes surfactants that maintain the monomer mixtures as a well distributed emulsion. The specific ingredients of the soap solution included Aerosol™ NPES 458 which is a 58% solution of the ammonium salt of sulfated nonylpoly (ethyleneoxy) ethanol and Aerosol™ 75, a 75% solution of sodium dioctyl sulfonate, both of which are manufactured by Cyanamid, and Disponil FES77, a 32.5% solution of sodium lauryl ether sulfate, manufactured by Henkel.

In addition to styrene, butyl acrylate, methyl acrylate, methacrylic acid, and acrylic acid, the first Monomer Mix included RC 726, a silicone acrylate manufactured and sold by Goldschmidt, and the silicones SL 6000-D1 and SL 6010-D1, both manufactured and sold by General Electric. The first Monomer Mix further included Ebecryl 270, an aliphatic urethane oligomer from Radcure. The second Monomer Mix included styrene, butyl acrylate, methyl acrylate, methacrylic acid, acrylic acid, SL-6000-D1, and Ebecryl 270.

A reactor which had first been purged with nitrogen was then charged with the Initial Reactor Charge at 68° C., and the contents were mixed for 5 minutes. The first pre-emulsion monomer mixture was then slowly introduced into the stirred reactor over a two hour period. After about one-sixth of the first pre-emulsion mix had been added to the reactor (after about 20 minutes) the addition of the first Catalyst/Activator solution into the reactor was started and continued along with the addition of the remainder of the first Monomer Mix. The Catalyst/Activator solutions included potassium persulfate as the catalyst and sodium metabisulfite as the activator for the Monomer Mixes.

Once the first Catalyst/Activator solution and first Monomer Mix had been added to the reactor, the temperature of the reactor was maintained at 68° C.±2° C. for about 15 to 20 minutes. While not wishing to be bound by theory, it is applicant's belief that this first Monomer Mix reacts to form the polymeric core of the core and shell polymers used in forming the coating material of the present invention.

As the second step in the sequential polymerization step, the second pre-emulsion feed was slowly introduced into the reactor over the course of two hours. As was done with the first Catalyst/Activator solution, the introduction of the second Catalyst/Activator solution was started after one-sixth of the second Monomer Mix had been introduced (after 20 minutes) into the reactor. During the addition of the second Monomer Mix and the second Catalyst/Activator solution, the reactor temperature was maintained at 70° C.±3° C. It is important during this step that the temperature not exceed about 73° as such temperatures can cause decomposition of the redox agents in the mixture. While not wishing to be bound by theory, it is applicant's belief that the second Monomer Mix reacts to form the shell of the core and shell polymers described above.

Once the entire second Monomer Mix and second Catalyst/Activator solution had been introduced, the reactor temperature was raised to 75° C. and the temperature was held between 73° C. and 78° C. for about 1.5 to 2 hours. At the end of this period, the Rinsing Solution was added to the reactor. In addition to rinse water, the Rinsing Solution included a 28% ammonia solution which neutralizes the pH of the acidic polymerization reaction product, Drewplus L-191, a defoaming agent manufactured and sold by Drew Industrial Division of Ashland Chemical Company (Boonton, N.J.) and Kathon LX, a biocide manufactured and sold by Rohm & Haas Company, Inc., (Philadelphia, Pa.).

The above protocol was repeated for each of Examples 2 to 4 to make four different copolymer emulsions.

EXAMPLES 5–8

Natural Latex Rubber Glove Manufacture.

For Example 5, calcium nitrate was added to the copolymer emulsion of Example 1, which was then coated onto a mold for making an examination glove. The coated mold was immersed into a pre-cured natural rubber latex solution and allowed to remain in the solution until a coat of 6 to 10 mils built up on the coating. The coated mold was then leached and immersed in a solids suspension of the Example 1 copolymer. After curing and cooling, the glove was stripped from the mold.

The glove formed was pinhole-free and had matte inner and outer surface. The copolymer was strongly bonded to the latex, and the formed glove had excellent dry donning properties for use as an examination glove. No flaking occurred when the glove was stretched. FIG. 6 shows the DSC profile for the copolymer, with major glass transition temperature peaks at about −50° C., −39° C., −20° C. and 31° C. Surface morphology revealed a slightly irregular continuous surface with microcraters and submicron protrusions, the microcrater diameters ranging from 0.1 to 1 micron.

For Examples 6–8, this procedure was repeated, using the copolymer emulsions of Examples 2–4. Results similar to those for Example 5 were achieved.

EXAMPLES 9–16

Neoprene and Nitrile Rubber Glove Manufacture.

For Examples 9–12, the procedure of Examples 5–8 was followed except that instead of forming an examination glove from an emulsion of pre-cured natural rubber latex, a glove was formed from a neoprene latex rubber emulsion. These gloves had excellent donning properties.

For Examples 13–16, the procedure of Examples 5–8 was followed except that instead of forming an examination glove from an emulsion of pre-cured natural rubber latex, a glove was formed from a nitrile latex rubber emulsion. Another difference was that only a donning coating was applied as mold release is not generally a problem for articles molded from nitrile rubber latex. As with the other examples, these gloves had excellent donning properties.

This invention in its broader aspect is not limited to the specific details shown and described herein. Departures from such details may be made without departing from the principles of the invention and without sacrificing its chief advantages. As used herein, use of the word "about" in relation to a range of values is intended to modify both the high and low values recited.

What is claimed is:

1. A copolymer composition formed for use as a coating for rubber articles, formed of a mixture of monomers comprising:
   at least one low surface energy monomer selected from the group consisting of copolymerizable silicone oligomers, fluorocarbons, and fatty acid esters, and having a functionality selected from the group consisting of vinyl, acrylic, and methacrylic functionalities;
   at least one alkyl acrylate having 1 to about 10 carbon atoms in the alkyl group;
   at least one urethane oligomer; and
   at least one hard monomer.

2. A copolymer composition as recited in claim 1, wherein the at least one alkyl acrylate is selected from the group consisting of methyl acrylate, butyl acrylate, and mixtures thereof.

3. A copolymer composition as recited in claim 1, wherein the at least one urethane oligomer is a diacrylate urethane oligomer.

4. A copolymer composition is recited in claim 1, wherein the at least one hard monomer is selected from the group consisting of styrenic monomers, alkyl methacrylates, unsaturated carboxylic acids containing 3 to 4 carbon atoms, acrylic and/or methacrylic amides, and mixtures thereof.

5. A copolymer composition as recited in claim 1, wherein the mixture of monomers comprises, on a percent by weight basis, based on the total weight of monomers,
   about 0.7% to 20% low surface energy monomer(s);
   about 30% to 80% alkyl acrylate(s);
   a positive amount up to about 10% urethane oligomer(s);
   and a positive amount up to about 45% hard monomer(s).

6. A copolymer composition as recited in claim 1, wherein the mixture of monomers comprises at least one copolymerizable silicone oligomer; at least one alkyl acrylate selected from the group consisting of methyl acrylate, butyl acrylate, and mixtures thereof; at least one urethane oligomer; and at least one hard monomer selected from the group consisting of styrenic monomers, methacrylic acid, acrylic acid, itaconic acid, methyl methacrylate, isobutoxymethacrylamide, isobutylmethacrylate, and mixtures thereof.

7. A copolymer composition as recited in claim 1, formed in the presence of a surfactant system comprising at least two anionic surfactants.

8. A copolymer composition as recited in claim 7, wherein the surfactant system comprises at least two of sodium dioctyl sulfosuccinate, the ammonium salt of a sulfonated nonylphenoxypoly(ethyleneoxy) ethanol, or a fatty alcohol polyglycol ether sulfate.

9. A copolymer composition as recited in claim 1, prepared by sequential polymerization of at least two monomer mixtures, at least one of which comprises at least one silicone oligomer, at least one alkyl acrylate, at least one urethane oligomer, and at least one hard monomer.

10. In a copolymer composition formed for use as a coating for rubber articles, prepared by copolymerization of a mixture of monomers including, on a percent by weight basis based on the weight of all monomers, about 0.7 to 20% of at least one low surface energy monomer, about 30 to 80% of at least one alkyl acrylate having one to ten carbon atoms in the alkyl group, and up to about 40% of at least one hard monomer, the improvement comprising a positive amount up to about 10% by weight of at least one urethane oligomer in the mixture of monomers.

11. An improved composition as recited in claim 10, where in the urethane oligomer is present in an amount of about 3% to 5% by weight, based on the weight of all monomers.

12. An improved composition as recited in claim 10, wherein the urethane oligomer is present in an amount of about 3.8% by weight, based on the weight of all monomers.

* * * * *